United States Patent
Anderson

(10) Patent No.: US 8,858,927 B2
(45) Date of Patent: Oct. 14, 2014

(54) METHOD FOR PROTECTION OF PEPTIDES OR PROTEINS AGAINST NON-ENZYMATIC DEAMIDATION

(75) Inventor: David Anderson, Ashland, VA (US)

(73) Assignee: Lyotropic Therapeutics, Inc., Ashland, VA (US)

( * ) Notice: Subject to any disclaimer, the term of this patent is extended or adjusted under 35 U.S.C. 154(b) by 598 days.

(21) Appl. No.: 12/809,206

(22) PCT Filed: Dec. 19, 2008

(86) PCT No.: PCT/US2008/087611
§ 371 (c)(1),
(2), (4) Date: Aug. 27, 2010

(87) PCT Pub. No.: WO2009/086062
PCT Pub. Date: Jul. 9, 2009

(65) Prior Publication Data
US 2010/0316606 A1    Dec. 16, 2010

Related U.S. Application Data

(60) Provisional application No. 61/122,789, filed on Dec. 16, 2008, provisional application No. 61/015,993, filed on Dec. 21, 2007.

(51) Int. Cl.
*A61K 45/00*    (2006.01)
*A61K 38/21*    (2006.01)
*A61K 39/395*   (2006.01)
*A61K 9/00*     (2006.01)
*A61K 9/19*     (2006.01)
*A61K 47/26*    (2006.01)
*A61K 47/20*    (2006.01)

(52) U.S. Cl.
CPC ............ *A61K 9/0019* (2013.01); *A61K 9/0048* (2013.01); *A61K 9/19* (2013.01); *A61K 47/26* (2013.01); *A61K 47/20* (2013.01)
USPC .... 424/85.1; 424/85.4; 424/130.1; 424/141.1

(58) Field of Classification Search
None
See application file for complete search history.

(56) References Cited

U.S. PATENT DOCUMENTS

| | | | | |
|---|---|---|---|---|
| 6,013,773 | A * | 1/2000 | Kobayashi et al. | ............ 530/399 |
| 6,274,553 | B1 * | 8/2001 | Furuya et al. | ................ 514/14.8 |
| 2003/0092622 | A1 | 5/2003 | Sato et al. | |
| 2006/0234989 | A1 | 10/2006 | Anderson | |

OTHER PUBLICATIONS

Cournoyer et al., Analysis of Deamidation in Proteins, Comprehensive Analytical Chemistry, 52, 375-410, 2009.*
Wright T. H., Nonenzymatic Deamidation of Asparaginyl and Glutaminyl Residues in Proteins, Crit. Rev. Biochem. Mol. Biol. 26, 1-52, 1991.*
Potter, S., et al. "In vitro aging of calmodulin gnerates isoaspartate at multiple Asn—Gly and Asp—Gly sites in calcium-binding domans II, III, and IV"; Protein Science (1993), 2, pp. 1648-1663.
Nilsson, M., et al., "Low levels of asparagine deamidation can have a dramatic effect on aggregation of amyloidogenic peptides: Implications for the study of amyloid formation"; Protein Science (2002) 11, pp. 342-349.
Perna, A., et al., "Plasma protein aspartyl damage is increased in hemodialysis patents: Studies on causes and consequences"; J. AmSoc. Pephrol. (2004)15, pp. 2747-2754.
Paleari, R., et al., Posttranslational deamidation of proteins: the case of Hemoglobin j sardegna [alpha50(CD8)His>Asn>Asp]; Clinical Chemistry, 45:1, Molecular Diagnostics and Genetics (1999) pp. 21-28.
Robinson, N., et al., "Predictin of primary structure deamidation rates of asparaginyl and glutaminyl peptides through steric and catalytic effects"; J. Peptide Res., 2004, 63, 437-448.
Cloos, P., et al., "Post-translational modifications of proteins: implications for aging, antigen recognition, and autoimmunity"; Biogerontology 5: (2004); pp. 139-158.
Wakankar, A., et al., "Formulation considerations for proteins susceptible to asparagine deamidatino and aspartate isomerization"; J. of Pharm Sciences, vol. 95, No. 11,(2006) pp. 2321-2336.

* cited by examiner

*Primary Examiner* — Elly-Gerald Stoica
(74) *Attorney, Agent, or Firm* — Whitman Curtis Christofferson & Cook, PC

(57) ABSTRACT

Stabilization of water-containing solutions or lyophilizates of proteins and peptides against non-enzymatic deamidation degradation reactions at asparaginyl or glutaminyl residues is achieved using organic anions, such as saccharin, benzenesulfonic acid, gentisic acide or N-acetyltryptophan which have a pKa within the range of 0.5 to 3.5.

21 Claims, 1 Drawing Sheet

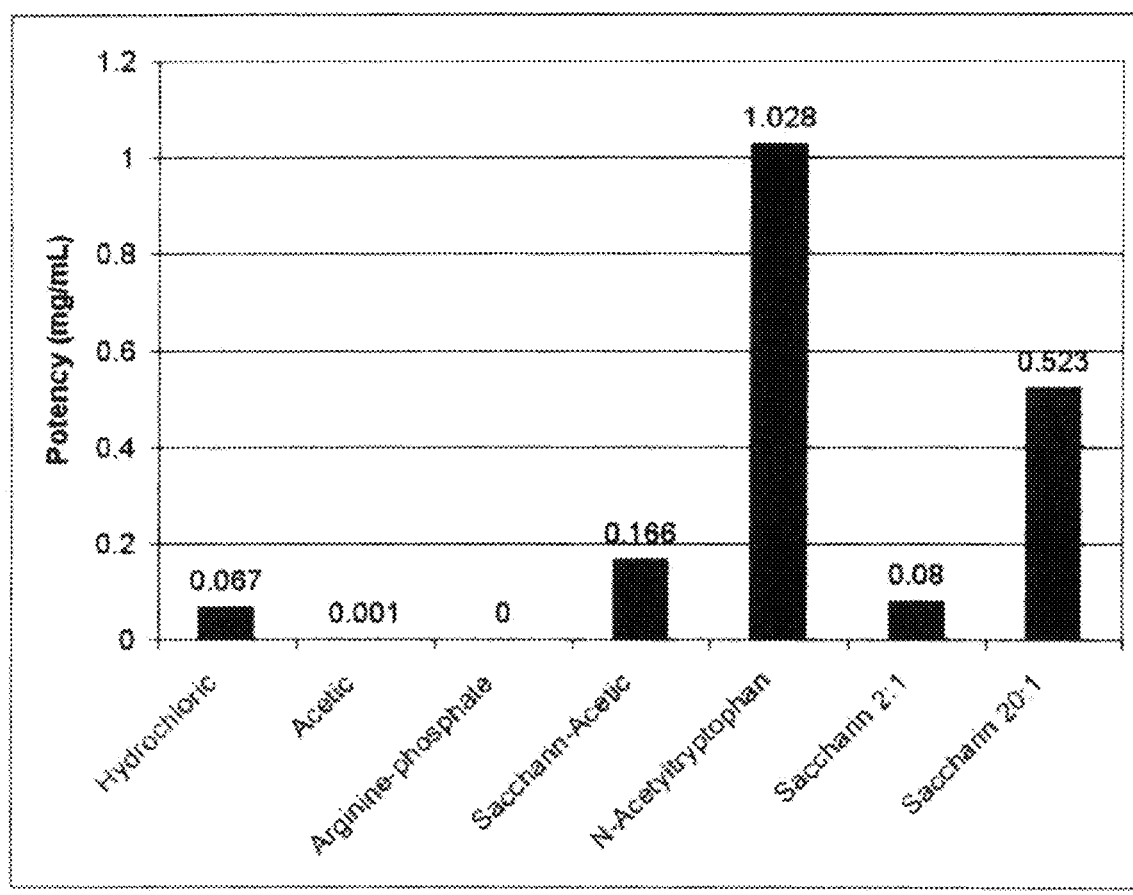

METHOD FOR PROTECTION OF PEPTIDES OR PROTEINS AGAINST NON-ENZYMATIC DEAMIDATION

CROSS-REFERENCE TO RELATED APPLICATIONS

This application is a national stage application based on PCT/US2008/087611 filed Dec. 19, 2008, and claims priority to U.S. Provisional 61/122,789 filed Dec. 6, 2008 and U.S Provisional 61/015,993 filed Dec. 21, 2007, and the complete contents thereof is herein incorporated by reference.

BACKGROUND

Peptides and proteins commonly undergo a type of degradation reaction known as deamidation. This reaction occurs at susceptible glutaminyl and, especially, asparaginyl residues. Deamidation can occur at or near neutral pH by the beta-aspartyl shift mechanism, as well as at high or low pH, thereby making it difficult to prevent by simple buffer adjustment. Indeed, it is well known that the ubiquitous buffer component phosphate ion accelerates deamidation reactions, for example.

Protein/peptide deamidation is fundamentally different from a simple hydrolysis reaction. The first step in base-catalyzed deamidation of a peptide or protein at an asparaginyl or glutaminyl residue is usually nucleophilic attack of the adjacent main-chain nitrogen on the carbonyl, giving off an ammonia molecule, to form a short-lived intermediate which is a succinimide (a cyclic imide); this contrasts with the case of a simple hydrolytic attack of say, an ester or amide, by a water molecule (or one of its constituents, a hydroxyl ion or proton); in the latter case, the water molecule attacks an intact compound, whereas in peptide deamidation, water can attack the succinimide after the nucleophilic attack, so that attack by water is not the initial step. The facts that 1) the susceptible groups are the amides on the asparaginyl and glutaminyl residues; and 2) the attacking atom is a nitrogen, underscore an even more fundamental difference between peptide deamidation on the one hand, and de-esterification of ester-containing small molecules on the other. It is well established that in base-catalyzed deamidation, the formation of the succinimide by the afore-mentioned nucleophilic attack is the rate-limiting step. The activation energy for deamidation of proteins and peptides is approximately 22 kCal/mol. Those asparaginyl residues that are most prone to deamidation are those flanked on their C-terminal side by either a glycinyl or serinyl residue: Asn-Gly or Asn-Ser sequences.

Deamidation of an asparaginyl residue, yielding either an aspartate or isoaspartate residue (or, in uncompleted form, a succinimide derivative), is a change in the primary structure of the protein or peptide, and often results in significant loss of activity in vivo (viz., in a pharmaceutical preparation) and/or in vitro (e.g., in a diagnostic or assay system). Furthermore, such degradation of proteins and peptides can lead to an increase in immunogenicity, which can have disastrous effects. Also, deamidation can create degradation products that trigger abnormal changes in intracellular levels of certain peptides/proteins. And while the body has enzymes that repair deamidation damage in some proteins, the need for treatment with biopharmaceutical drugs in some cases relates right back to defective machinery in the functioning of these repair enzymes, so that administration with a (partially) deamidated protein or peptide could aggravate the exact problem the drug is supposed to treat. Deamidation of peptides and proteins can increase their incidence of denaturation or fibrillation, make them more prone to proteases, or modify their binding characteristics (e.g., of an antibody). As a particularly important example, succinimide intermediates from the first stages of base-catalyzed deamidation (particularly in the case of the peptide amylin) are hypothesized to be directly responsible for amyloid deposits, and thus may play central roles in such diseases as Parkinson's disease, type II diabetes, prion disease, and possibly Huntington's disease.

Degradation via deamidation is one of the reasons why most biopharmaceuticals must be produced in lyophilized (freeze-dried) form, requiring reconstitution before injection or other administration. Insulin is an extremely important example of a self-administered, home use drug that is supplied as a ready-to-use aqueous solution, and human insulin contains three asparagine residues. Deamidation of insulin is a well-established phenomenon. Recombinant human DNAase and recombinant soluble CD4 are well-established to lose activity upon deamidation.

Furthermore, even lyophilized formulations are sometimes formulated at very low pH (or less commonly, high pH) in order to limit deamidation and related reactions. This is in some cases due to deamidation that would otherwise occur during storage, or in other cases would occur between reconstitution and administration. Formulations at extreme values of the pH, namely less than about 4 or especially less than or equal to about 3, are highly unphysiological and can cause local damage, extravasation of the drug, and other harmful effects. Furthermore, restricting the range of pH available for formulating a particular peptide or protein can make it more difficult or even impossible to achieve targeted solubility or to avoid gelation, denaturation, clumping, etc. US patent application 2002/0061838 to Holmquist and Normady describes compositions with pH values between about 3.0 and 5.0 that contain acids, primarily in protonated form (i.e., formulation pH below the pKa of the acid, typically acetic acid), at small molar concentrations (typically 10 mM), intended to prevent aggregation or gelation of the peptide.

In aqueous solutions, the solution viscosity has only a relatively small effect on deamidation rates. However, the glassy and semicrystalline states that occur with lyophilization can strongly reduce deamidation, and thus the usual approaches of optimizing reducing sugars, non-reducing sugars, and polyols are very useful. Nevertheless, even in such formulations, deamidation—or at least the initial succinimide formation—can still occur within the lyo cake during storage as well as in pre-lyophilization production steps, and in the period between reconstitution and administration, which can be many hours in some cases, such as up to 8 hours in the case of the Alteplase formulation marketed as Activase®. The polyols, sugars and other cake-modulating compounds do not participate chemically to modify the deamidation reaction, but act indirectly through physical effects on the protein medium. Indeed, their stated main purpose is taken to be their effects on stabilizing secondary and tertiary structures of peptides and proteins, by reducing mobility of molecules or chemical moieities. For example, noted expert in the field John F. Carpenter, in the book *Rational Design of Stable Protein Formulations: Theory and Practice* (2002, Springer, John F. Carpenter and Mark C. Manning, eds.) states "Finally we will address this and other practical issues in the use of stabilizing excipients to inhibit protein unfolding during freezing and drying . . . . Among the numerous compounds tested, it appears that the most effective stabilizers of proteins during lyophilization are disaccharides."

Human albumin solutions are used therapeutically as plasma volume expanders. Marketed albumin formulations for intravenous injection, such as Buminate® (Baxter Healthcare), Plasbumin® (Bayer Biological), and Human Albumin Grifols® (Grifols) contain equimolar amounts (1:1 molar ratio) of sodium caprylate and sodium N-acetyltryptophanate. The molar ratio of N-acetyltryptophan to albumin is 5.36:1, and since each albumin molecule has 17 asparaginyl residues, the ratio of N-acetyltryptophan to asparaginyl residues is 0.315:1. Shrake et al. [Vox Sang. 1984, 47(1), 7-18] have used differential scanning calorimetry to show that caprylate and acetyltryptophanate help prevent denaturation (disruption of protein secondary and/or tertiary structure) during the heat treatment step of albumin purification. Duggan and Luck [J. Biol. Chem. (1947) pp. 205-220] showed that these compounds—especially the caprylate—functioned by preventing viscosity rises in albumin solutions under conditions of denaturation with urea. According to that publication, "The comparative efficacy of stabilizers would then be determined by the mole ratio necessary to keep the viscosity of the albumin-urea system at its lowest value."

It is well established [e.g., Bischoff and Kolbe (1994) J. Chromatogr. B, vol. 662, p. 261] that the deamidation-prone asparaginyl residues are those flanked on their C-terminal sides by either glycinyl or serinyl residues (small amino acids), and albumin has no such residue. Furthermore in its therapeutic role as a plasma volume expander, albumin's beneficial effect against hypovolemia would probably not be detrimentally affected by deamidation even if it were to occur.

OctreoScan® is a diagnostic preparation for the injection of a radiolabelled peptide derivative that contains, per 10 mL of reconstituted peptide-derivative solution, 2 mg of gentisic acid, 4.9 mg of trisodium citrate, 0.37 mg of citric acid, and 10 mg of inositol. The stated purpose of the gentisic acid in this formulation is to inhibit autoradiolysis of the radiolabelled compound capable of existing at a stable oxidation state. The peptide in OctreScan is derivatized first by covalent attachment of 4 acetic acid groups, and before administration by binding of indium-111. The amino acids in the peptide portion of the compound are phenylalanine, cystine, threonine, and tryptophan; thus, no asparaginyl or glutaminyl residues are present. The active moiety, namely the indium-111 atom, is chelated within the grasp of the acetic acid groups, analogously with the binding of multivalent ions with EDTA (ethylenediamine tetraacetic acid).

A list of proteins and peptides that undergo deamidation (non-enzymatically) has been compiled. [See T. Wright, Amino Acid Abundance and Sequence Data: Clues to the Biological Significance of Nonenzymatic Asparagine and Glutamine Deamidation in Proteins, in: *Deamidation and Isoaspartate Formation in Peptides and Proteins*, D. Aswad Ed., CRC Press, 1995; see also Teshima et al. in: *Deamidation and Isoaspartate Formation in Peptides and Proteins*, D. Aswad Ed., CRC Press, 1995]. This compilation will be taken as authoritative in this disclosure.

Human growth hormone is known to undergo deamidation degradation during the period (up to 14 days) between reconstitution and administration. Addition of zinc ions helps to ameliorate this and other degradation mechanisms of hGH and of insulin. Zinc in these formulations is, of course, a divalent cation.

Whereas a number of means are known in the art for protecting proteins in aqueous solution against physical changes such as aggregation, gelation, denaturation, molten states, thermal transitions, and generally, changes in secondary or tertiary structure, as well as for other types of chemical changes such as disulfide bond breakage or crosslinking (which can also lead to significant changes in physical structure and properties), the art has been lacking in broadly-effective and pharmaceutically-acceptable ways to specifically hinder or prevent non-enzymatic deamidation of asparaginyl residues. Methods that stabilize secondary and tertiary structures of proteins and peptides may play an indirect role in inhibiting deamidation reactions in isolated cases—though there is no a priori reason why the native conformation is the most stable against deamidation—and the complexes that can be promoted by multivalent ions can retard diffusivities and mobilities and, again, indirectly reduce deamidation rates, though often at the price of reducing drug solubility. More direct and widely-applicable stabilization of asparaginyl residues through chemical means are lacking.

SUMMARY

It is an object of this invention to provide compositions containing deamidation-prone peptides and proteins which show significantly decreased rates of non-enzymatic degradation due to the presence of certain stabilizers.

It is a further object of this invention to provide stabilized aqueous solutions of proteins and peptides such that they can be supplied as ready-to-use formulations, preferably with at least 2 years shelf-life.

It is a further object of this invention to provide methods for stabilizing deamidation-prone peptides and proteins that are to be administered to human or animal patients or are to be used in diagnostics or other applications, and where the peptides and proteins are present in formulations an lyophilizates.

According to the invention, stabilization of water-containing solutions or lyophilizates of proteins and peptides against non-enzymatic deamidation degradation reactions at asparaginyl or glutaminyl residues is achieved using organic anions, such as saccharin, benzenesulfonic acid, gentisic acid or N-acetyltryptophan which have a pKa within the range of 0.5 to 3.5, and more preferably between 1.5 and 3.5. The stabilizing anions combined with the peptides or proteins are present in a molar excess to the total number of asparaginyl or glutaminyl residues in the peptides or proteins, and are in a molar excess to any destabilizing anions in said mixture. The stabilizing anions are organic compounds that are not zwitterionic where each protic group of said stabilizing anion has a pKa ranging from 0.5 to 3.5. The destabilizing anions, if present, have at least one protic group that has a pKa of less than 0.5 or greater than 3.5.

DESCRIPTION OF THE DRAWING FIGURE

FIG. 1 provides a bar graph summarizing some of the data in Examples 1 and 2.

DETAILED DESCRIPTION

Definitions

The following definitions will be useful in understanding the invention.

"Drug", "Active pharmaceutical ingredient": By "drug", or equivalently "active pharmaceutical ingredient", we mean the peptide or protein that is the active pharmaceutical compound—in the definition and spirit of the use of this term by regulatory agencies such as the FDA, which is in substantial accord with that of one skilled in the pharmaceutical arts—of a formulation that is acceptable for administration to a mammal, usually though not always a human, by one or more of said regulatory agencies. In this disclosure, if other peptides (or proteins) are present in the drug formulation besides the active drug, then the term "peptide" (or "protein") will refer to the active drug, and other, non-active peptides (or proteins) will be referred to as excipients regardless of their MW. In rare cases, a single formulation might contain more than one active peptide (or protein) drug. While the qualifier "biopharmaceutical" is often applied to an active pharmaceutical ingredient that is a peptide or protein, in the present context it will be understood that the drugs in question are biopharmaceutical even if the term "pharmaceutical" is applied.

"Protein", "peptide": These will refer to compounds whose functionality as a drug is primarily and centrally dependent on a sequence of amino acids joined by peptide bonds, as well known in the art. Generally, a peptide has an amino acid sequence less than about 5,000 MW, and a protein has greater than about 5,000 MW. In the present context, if an excipient (i.e., not the drug) in a drug formulation happens to be a protein or peptide, then this should be distinguished by referring to it as a "protein excipient" or "peptide excipient"; otherwise, the terms "peptide" and "protein" will be reserved for the active drug (or several active drugs) in a formulation.

"Endogenous", "exogenous": For the purposes of this disclosure, the active in a drug formulation will be considered endogenous if and only if it is present in the body of the mammal receiving the formulation prior to the formulation administration by virtue of the body's metabolism, such that it is maintained at significant levels in the body over time even in the absence of any administration of the drug; the drug must be similar enough to the compound maintained by body metabolism that the two are substantially identical in function, potency, metabolic fate, immune recognition, etc. Thus, for example, certain marketed forms of insulin are identical to human insulin except for a single amino acid substitution intended to increase stability, and provided this does not introduce immunogenicity or other changes, this would be considered endogenous in the current context. A drug is "exogenous" if and only if it is not endogenous in this sense. In view of the spirit of this disclosure, the degradation of an active (e.g., during its shelf-life) does not affect its "endogenous" status, i.e., the assignment of "endogenous" will be based on the un-degraded formulation.

"Deamidation-susceptible": A peptide or protein drug will be deemed "deamidation-susceptible" if, and only if, the deamidation rate constants of the asparaginyl residues on the molecule are sufficiently high that about 10% or more of the drug molecules will undergo at least one asparaginyl deamidation, or conversion to succinimide derivative, over a period of two years at 25° C. in aqueous solution at pH 7.4. This corresponds to a $T_{1/10}$ of 730 days, where $T_{1/10}$ is the industry-accepted symbol for the time at which 10% degradation occurs, in this case with specific focus on deamidation, in this case at 25° C. (The symbol is used, for example, in the Robinson & Robinson *Deamidation of Human Proteins* reference cited below). Equivalently, it corresponds to a rate constant (using a simple single-exponential reaction equation model) of $6.1 \times 10^{-6}$ $hr^{-1}$, at 25° C. In the event that several asparaginyl (or even glutaminyl) residues deamidate at comparable rates, then 10% deamidation of the overall peptide or protein (which only requires one deamidation reaction per molecule) might occur in less than 2 years even if the reaction constants are somewhat less than $6.1 \times 10^{-6}$ $hr^{-1}$, though at least one would inevitably have to be on the order of $10^{-6}$ $hr^{-1}$. For the purposes of Arrhenius analysis of reaction rates, as noted above the accepted value of the activation energy for deamidation should be close to 22 kCal/mol.

"Deamidation-prone": A peptide or protein drug will be deemed "deamidation-prone" if, and only if, the deamidation rate constants of the asparaginyl residues on the molecule are sufficiently high that about 10% or more of the drug molecules will undergo at least one asparaginyl deamidation, or conversion to succinimide derivative, in a period of two years at 4° C., i.e., $T_{1/10}$<730 days at 4° C., in a pH 7.4 solution.

"pKa": The pKa of an acidic group will be taken to be that used in the chemical arts, namely the negative logarithm of the dissociation constant for a dilute aqueous solution of the acid, or more functionally as the pH at the inflection point in the acid-base titration curve. According to the Henderson-Hasselbach equation, when the pH of a dilute solution of the acid is equal to the pKa, 50% of the acid is deprotonated. A single compound can have several groups, each with an assigned pKa. Reasonable, accepted approximate values for the pKa(s) of a number of acids pharmaceutically-acceptable as excipients are as follows: acetic, 4.7; citric, 3.13, 4.76 and 6.40; phosphoric, 2.2, 7.9 and 12.3; ascorbic, 4.17 and 11.6; lactic, 3.95; maleic, 3.9; tartaric, 2.96 and 4.24; oleic, 4.5; benzenesulfonic, 0.7; N-acetyltryptophan, 3.37; gentisic, 2.9; saccharin, 2.0; glycocholic, 3.6; deoxycholic, 5.7; hydrochloric, −7. The uncertainty is highest on those acids with the lowest pKa values, and those with the lowest solubilities. In cases, such as deoxycholic acid, where the pKa depends strongly on concentration, then the pKa at the concentration used in the (possibly prospective) formulation under consideration is the operative pKa. The pKa is determined experimentally by methods well known to one skilled in the art, such as potentiometric titration, etc.

"Stabilizing anion": for the purposes of this invention, a stabilizing anion is an organic acid—either in protonated, or deprotonated form—that satisfies the criteria provided herein to make it functional, or at least potentially functional, as a stabilizer against protein or peptide deamidation (or any of the stages of the deamidation process, such as the formulation of a succinimide derivative as discussed herein). The primary criterion required for an acid or deprotonated acid to qualify as a "stabilizing anion" is that it have a pKa in the proper range, or, in the event it has more than one protic group, that substantially all of the protic groups on the molecule are acidic with pKa's in the proper range, specifically in the range of about 0.5 to about 3.5, and more preferably between 1.5 and 3.5; thus, amino acids, peptides and proteins themselves are generally not stabilizing anions, due to protic amino and other groups. Preferred stabilizing anions satisfy more preferred ranges of pKa and/or preferred ranges of carbon number. When discussing stabilizing anions, these are referred to interchangeably as "anions" or "acids", recognizing the fact that the proportion of the acidic (protonated) and anionic (deprotonated) forms of the molecule are determined by the pH of the solution in relation to the pKa(s) by formulae well known to one skilled in the art (and recognizing that each molecule is in dynamic equilibrium between the two forms). Notwithstanding this, it is preferred in the practice of the invention for the pH of the formulation to be at least 0.5 pH points, and more preferably, 1 pH point, above the pKa of the stabilizing compound in order for that stabilizer to be predominantly in the anionic (deprotonated) form.

"Destabilizing anion" (or "Detrimental anion"): Very surprisingly, it was found in the course of this work that acids and their associated anions (i.e., their conjugate bases) that have pKa values above about 3.5 are actually detrimental to stability, not only accelerating deamidation but even reducing or, at sufficient concentrations, negating the stabilizing effect of the stabilizing anions as defined above. As discussed elsewhere herein, molecules that have more than one anionic group are usually destabilizing anions, unless all the anionic groups have pKa's in the preferred range of 0.5-3.5, and more preferably between 1.5 and 3.5, which is very rare, due to neighboring group effects, the relatively small stable of pharmaceutically-acceptable excipients, and other factors. Destabilizing anions, which are to be minimized or (more preferably) avoided in the practice of the invention, include citrate, phosphate, malate, maleate, tartrate, benzoate, succinate, glucuronate, sorbate, and ascorbate, as well as fatty acids and their salts, such as sodium acetate, sodium caprylate, or sodium oleate. The fact that acetate (acetic acid, equivalently) is detrimental to asparaginyl stability is a very important discovery in this work, and is shown dramatically in Example 1 below.

"Pharmaceutically-acceptable": In the context of this invention, "pharmaceutically-acceptable" designates compounds or compositions in which each excipient is approved by the Food and Drug Administration, or a similar body in another country, for use in a pharmaceutical or vaccine formulation, or belongs to a succinct class of compounds for which a Drug Master File is on file with a government regulatory agency, usually the FDA, or, less preferably, is known from extensive toxicity studies to be safe for the intended route of administration (which in the context of this invention is typically, though not always, parenteral). This also includes compounds that are major components of approved excipients, which are known to be of low toxicity taken internally. A listing of approved excipients, each with the various routes of administration for which they are approved, was published by the Division of Drug Information Resources of the FDA in January, 1996 and entitled "Inactive Ingredient Guide". The existence of a Drug Master File at the FDA is additional evidence that a given excipient is acceptable for pharmaceutical use, at least for certain routes of administration. For injectable products, a listing of approved excipients was published in 1997. See Nema, Washkuhn and Brendel (1997) PDA *J. of Pharm. Sci. & Technol.* 51(4):166. It should be added that there are certain compounds, such as vitamins and amino acids, which are in injectable products (typically for parenteral nutrition) as "actives", and are thus known to be safe upon injection, and such compounds are considered herein as pharmaceutically-acceptable as excipients as well, for injection. All of the embodiments of this invention are understood to be pharmaceutically-acceptable for at least some route of administration in humans, meaning that every excipient in each embodiment is approved for use in humans, in at least one route of administration. This is crucial not only for product safety but also for utility of the invention, as a key feature of the invention is that it uses, preferentially, only FDA-approved excipients, most of which are in fact approved for injection. Examples of compounds that are not pharmaceutically-acceptable are taurocholic acid and its salts (not acceptable for any route of administration), dichloroacetic acid, sodium p-chlorobenzenesulfonate, and other N-acetylated amino acids besides N-acetyltryptophan. The surprising recognition that deamidation-stabilizing formulations can be found and produced within the narrow range of pharmaceutically-acceptable formulations is a key aspect of this invention, particularly as it recognizes the destructive effects of anions that do not fit the preferred range of pKa as described herein.

"Saccharin": To avoid any confusion, it is pointed out that in spite of the name—saccharin, which sounds like it should be related to saccharides—and the sweet taste, saccharin is not a polyol, nor any kind of sugar. The name reflects only the sweetness, not the chemical structure. The chemical structure is in fact 2,3-dihydro-3-oxobenzisosulfonazole ($C_7H_5NO_3S$).

Description

Surprisingly, in the course of experimental work by the inventor supported by theoretical considerations, and exemplified by the Examples below, it was found that asparaginyl stability of peptide (or protein) solutions containing organic anions drops off sharply above an anion pKa of about 3.5, and that for pKa values equal to or greater than about 3.5 the organic anion can actually destabilize the drug. A dramatic cutoff between stabilization and destabilization at the pKa value of 3.5 was reported by the inventor in connection with a small-molecule de-esterification hydrolysis reaction, in U.S. patent application Ser. No. 11/404,109. Since at the solution pH value of preferred embodiments of the invention, at least 90% of the organic anion is deprotonated, and since the amount protonated (i.e., in acid form) decreases in the more effective (lower pKa) cases, this trend is almost certainly not strongly dependent on the pH of the solution (provided it is not too strongly acidic), but rather, is largely independent of pH and thus "universal" in some sense. Hence, quite broadly, a pKa equal to or less than about 3.5 is strongly preferred in the practice of this invention. A less dramatic, though significant, drop-off in stabilizer effectiveness is also observed as the pKa drops down to negative values. Thus, saccharin, benzenesulfonic acid, N-acetyltryptophan and gentisic acid are strongly preferred in this invention, and much preferred over compounds above pKa 3.5 such as or acetic or citric acid, which are actually destabilizing. The destabilizing effect of acetate ion, for example, with its pKa of 4.5, is demonstrated in Example 1 below. Without wishing to be bound by theory, when a destabilizing anion (with pKa greater than 3.5) is present in molar concentrations about equal to or greater than that of the preferred anion (with pKa less than or equal to 3.5), it may compete with the preferred anion for binding to the labile group (viz., at the carbonyl carbon of the labile group), and effectively displace it because it is a poorer leaving group, thereby rendering the preferred anion far less effective, if not substantially ineffective.

Organic anions that have two acidic/anionic groups may need to be treated in the same way as mixtures of anions. In particular, one destabilizing acidic group, with a pKa greater than about 3.5, might nullify the stabilizing effect of an acidic group on the same molecule with a pKa less than or equal to 3.5. Thus, for example, tartaric acid, with a $pKa_1$ of 2.93 and a $pKa_2$ of 4.23, will not afford effective stabilization in the context of this invention. This is apparently related to the fact that the weaker acidic group (higher pKa) forms a stronger conjugate base than does the stronger acidic group. For a similar reason, phosphoric acid is a destabilizing anion in the context of this invention. In this evaluation of organic anions, any titratable acidic group with a pKa that is too high to be relevant should be removed from consideration, in particular if the pKa is more than about 1 pH point above the pH of the formulation.

Organic zwitterions behave, not surprisingly, very differently from the organic anions within the context of the current invention, and the effect of an acidic group with a pKa within the preferred ranges of the invention is largely nullified by the cationic moiety in the zwitterion. Thus, while the acidic group on a typical amino acid, for example, is between 2.0 and 2.5, and so well within the preferred range, the zwitterionic amino acids are not effective as stabilizers and are not to be deemed as organic anions of the invention; this is not necessarily true for acidic amino acids such as aspartic acid and glutamic acid.

Without wishing to be bound by theory, one explanation for stabilizer effectiveness when the pKa of the stabilizer is in the preferred range of 0.5-3.5, and particularly in the most preferred range between 1.5 and 3.5, is that the conjugate base may form a temporary covalent bond, or other type of complex, with the carbonyl carbon of the labile group on the peptide or protein, at least a fraction of the time, limiting access of the carbonyl to other nucleophilic attack. This is driven by the susceptibility of the carbon atom on the carbonyl group to nucleophilic attack, and in nucleophilic attack on carbonyl groups generally, reactivity correlates fairly strongly with basicity. If the pKa of the acid is too low, then the conjugate base is extremely weak, and will less frequently attack the carbonyl group. Thus, a stabilizer such as saccharin has a confluence of favorable characteristics for good stabilization in the context of this invention, namely a pKa low enough to yield the conjugate base (anion) as a good leaving group at or near physiological formulation pH, but not so low a pKa to make for a weak conjugate base. An anion with too low a pKa (below 1.5, and particularly below 0.5) will be content to exist as a solitary, hydrated anion. The stabilizer of the invention thus has reasonably high reactivity toward the carbonyl, but also high lability, that is, it is a good leaving group. The preferred pKa range given herein is the single best indicator of these properties. The temporary covalent bond, or similar complex, postulated to be responsible for the stabilizing effect in the invention should be thought of as forming, breaking, and reforming on a very fast timescale.

The present invention does not involve permanent covalent modification of peptides with the stabilizers. On the contrary, the formulations described herein work to leave the original peptide intact and unmodified. Upon administration to the body, by the time the peptide (or protein) reaches the site of action (typically a receptor protein or enzyme), the stabilizer and peptide have substantially separated and have little or no interaction, at least relative to the level of interactions that had occurred in the drug formulation (i.e., in the vial, or pill, capsule, etc.).

Excipients such as cyclodextrins that form long-lived complexes with a desired peptide or protein drug are substantially different from the preferred stabilizers of this invention, since the former can have such an "encapsulating" effect that it affects drug pharmacokinetics. Altered drug kinetics, such as delayed onset for anesthetics such as propofol, have been reported for cyclodextrin-drug complexes. In any case, cyclodextrins such as methyl-beta-cyclodextrin (MetβCD) are aprotic, in contrast with the anions of this invention. As discussed in the previous paragraph, a key aspect of this invention is that the stabilized formulations that are embodiments of the invention preferably exhibit substantially the same drug pharmacokinetics as the same formulation without the stabilizer(s). For example, the action of the stabilized formulation of a preferred embodiment is sufficiently identical to that of the same formulation minus the stabilizer(s) that the former would pass as bioequivalent to the latter according to the accepted definition of bioequivalence in pharmaceutics, well known and established in the art.

One important application of the instant invention is to allow formulation of a deamidation-prone peptide or protein at a pH that is closer to physiological (7.4) than would otherwise be possible. For pH greater than about 4, deamidation is base-catalyzed, and thus the form of deamidation that is reduced in the current invention is base-catalyzed deamidation—with the understanding that other base-catalyzed degradation reactions can also be reduced by the invention. The dramatic improvement of stability seen in Example 1 below indicates that use of the invention could allow for an increase of formulation pH by 1, or 2, or possibly even 3 pH points. Thus, for example, a peptide that would otherwise require a formulation pH of 3.5—very detrimental to the product profile, and in many cases to drug solubility—could with this invention be formulated well above 4, and thus only mildly acidic. Or, a peptide that would otherwise be essentially impossible to formulate can be formulated with the use of the invention, albeit possibly at an acidic pH such as 3.5 or 4.

An important embodiment of the instant invention applies to solution formulations containing water as a predominant component, with water greater than or equal to about 75% of the formulation by weight, and generally greater than about 90%. It is important to note that a given method or composition which is effective in hindering deamidation reactions for dry or low-moisture formulations (especially lyophilized formulations) may not apply to aqueous formulations, as this is a much higher stability hurdle, due to high mobilities that yield higher reaction rates for virtually any type of degradation reaction, deamidation or other. Nonetheless, the Examples given herein demonstrate that even in dilute aqueous solutions, the invention can be a very powerful way to stabilize peptides and proteins against deamidation, a ubiquitous form of change of the primary structure of peptides and proteins.

The invention thus helps protect directly against changes in primary structure, in particular against changes of deamidation-susceptible asparaginyl residues to aspartate or isoaspartate. Notwithstanding that, the invention may in some cases help protect against changes in secondary or tertiary structure, for example indirectly by virtue of stabilizing against chemical reactions such as in particular deamidation, or by concomitantly effecting changes in local viscosities, mobilities, hydrophobicities, etc. Indeed, one can imagine an embodiment of the invention where a stabilizer is found, or synthesized anew, that combines the deamidation-inhibiting effects of the stabilizers of focus in this invention with physical stabilization of secondary or tertiary structure. For instance, a compound could be produced by starting with a polyhydric alcohol, say glycerol, which is known to be a structural stabilizer of many proteins, and incorporate an anionic group that has a pKa in the preferred range of the invention, and employ this compound according to the teachings herein, viz., at the proper molar ratio to the deamidation-prone groups and in the (relative) absence of detrimental (destabilizing) anions, at a formulation pH at which the stabilizer is predominantly in deprotonated form and effective.

Many of the applications of the invention for protein and peptide drugs will be in injectable, and in particular intravenous, products where safety and amounts of injected excipients are critical issues. Therefore, one important favorable feature of the invention is that it involves small levels and amounts of additional excipients, namely the stabilizing anions. To achieve a molar excess of 200%, for example, in the context of a protein drug calls for only very small amounts of organic anion, because of the (generally) high molecular weights of the drugs, and low frequency of deamidation-prone subsequences. It is preferred, in fact, that the usual minimum effective dose recommended for the drug formulation contain less than about 100 mg of total organic anion additive(s) of the invention, and more preferably less than about 25 mg.

In case the pH of the formulation is not at least one pH point above the pKa of the stabilizer, the calculation of molar excess should be based not on the full amount of stabilizer present, but rather on the amount of stabilizer that is in anionic, deprotonated form. The fraction that is deprotonated is calculated from the Henderson-Hasselbach equation. Thus, for example, if the pH were equal to the pKa of the stabilizer, one would take the "active" portion of stabilizer to be one-half that of the full amount present, in calculating the molar excess, or the molar ratio.

It should be noted that in embodiments of the invention in their ready to use (e.g., reconstituted, or solution formulation)

forms, the stabilizing anion concentration will almost always be far too low to have any significant effect on solution viscosity. In such cases, the mechanism of protecting the primary structure of the protein or peptide does not depend in any way on viscosity modulation or other physical stabilization. It cannot be emphasized strongly enough that the amide side-chain stabilization that is the core of this invention is due to a specific chemical interaction between stabilizer and the side-chain amide, not to a non-specific physical interaction between stabilizer and domains of the peptide or protein.

Application of the invention to a drug formulation can allow for storage at room temperature (20-25° C.) where refrigeration (2-8° C.) or even reconstitution may otherwise be required, which for the case of protein formulations is frequently the case. Ready-to-use formulations as per the invention not only save the production costs associated with lyophilization (or other drying process), but also in clinical use, help minimize delays and costs in drug administration, dangers associated with calculation errors in reconstituting and dosing, and dangerous precipitation if the wrong diluent is used. In some cases, the invention might substantially prolong the time allowable between reconstitution of a dried formulation and administration of the reconstituted formulation, compared to that in the absence of the stabilizing anion of the invention. For example, the invention could be used to protect the active after reconstitution for the case of the protein uracil-DNA glycolase (1LAU), which loses 10% potency in about 3.6 hours in pH 7.4, 37° C., 0.15 M Tris•HCl buffer, as does uroporphyrinogen decarboxylase (1URO). Example 1 below shows another case where a peptide degrades on a timescale of hours, and where application of the instant invention greatly inhibits this degradation. In the application of the instant invention to protection of a peptide or protein drug after reconstitution and before administration, there are two ways in which the stabilizers of the invention can be applied. First, it can be incorporated into the solution that is dried (usually by lyophilization), thereby becoming a permanent part of the dried formulation; in this method, the stabilizer may also help stabilize the drug in the dried state, since traces of water (or in some cases significant amounts, even in excess of 1%) will always remain, and can pool; furthermore, the early steps of deamidation may not require water at all, so the invention may protect drug integrity even in a well-dried lyophilate. Or second, it can be incorporated into an aqueous solution used to reconstitute the dried powder. The latter method has the advantage that the additive is not present during lyophilization, and so its potential effect on lyophilization need not be a concern. Thus, the method of reconstituting a dried protein or peptide solution with an aqueous solution containing a stabilizing anion as described herein is one aspect of the invention.

Additionally, since many peptide or protein drugs are administered by subcutaneous, intramuscular, or other "depot" routes where the formulation might sit for minutes or hours relatively intact (and perhaps even relatively undiluted), and during that time be prone to deamidation, then the invention could be used as described in the previous paragraph—even in cases where the time between reconstitution and administration is negligible from a degradation perspective. Such routes include subcutaneous; intramuscular; intraperitoneal; topical; ophthalmic; otic; intranasal; intravaginal; intrathecal; epidural; intravitreal; intracisternal (CSF of brain); intrathoracic; bladder instillation; local depot release such as exemplified by the Gliadel Wafer; and in long-circulating microcapsules. Focusing in on ophthalmic applications, the invention could be applied through a wide range of ophthalmic routes: periocular, intraocular, conjunctival, sub- conjunctival, transconjunctival, peribulbar, retrobulbar, sub-tenons, transscleral, intraorbital, intrascleral, intravitreal, subretinal, transretinal, choroidal, uveal, intracameral, intracorneal, intralenticular, and in or adjacent to the optic nerve.

Use of the invention could substantially reduce the risk of adverse reactions to a protein formulation caused by deamidation. Such reactions include anaphylaxis, various side-effects, immunogenicity, autoimmunity, and possibly conditions related to such diseases and celiac disease or senile cataractogenesis, where deamidation is believed to play an important role in disease development. Other adverse reactions associated with deamidation are discussed elsewhere herein. Use of the invention could also prevent or substantially reduce changes in the pharmacokinetics, or biodistribution, of a protein drug due to deamidation.

In addition to storage, the invention could be used to hinder deamidation in antiviral heat treatments used in biopharmaceutical processing, as well as in other stages of biopharmaceutical production. In addition, embodiments of the invention may include ready-to-use, aqueous formulations pharmaceutically-acceptable for injection under the requirement of two years stability that are at a formulation pH which is closer to physiological (7.4 for man) than would be possible without the invention. Thus, while many proteins must be formulated at pH values that are non-physiological and may result in local irritation or other noxious effect, the current invention may allow formulation of these proteins preferred range of about 3.5 to 9.5, or more preferably in the range of greater than 5.0 and less than about 9.0.

Due to potentially grave consequences from deamidation of protein drugs, it is particularly important that other organic, or inorganic, acids not meeting these criteria are avoided or at least limited. Such destabilizing anions which are to be minimized or (more preferably) avoided in the practice of the invention include, but are not limited to, citric, phosphoric, malic, maleic, tartaric, benzoic, succinic, glucuronic, sorbic, acetic, and ascorbic acids, as well as fatty acids and their salts, such as sodium acetate, sodium caprylate, or sodium oleate. Since peptides and especially proteins typically have buffer and/or ionic strength requirements in solution, the practice of the invention in these cases demands careful attention to the fact that many common buffer components and salts interfere with the stabilizing effect of saccharin and the other stabilizers disclosed herein. In particular, the total molar concentration of any of these destabilizing ions present should be less than the total molar concentration of the stabilizing anion(s) (saccharinate, benzenesulfonate, N-acetyltryptophanate, gentisate acid, etc.) of the invention, preferably less than or equal to about one-half the molar concentration of the stabilizing anion(s), more preferably less than one-third, and most preferably less than or equal to about one-tenth the molar concentration of the stabilizing anion(s) of the invention. Phrased otherwise, the molar ratio of stabilizing anions to destabilizing anions should be preferably greater than or equal to about 2:1, more preferably greater than or equal to about 3:1, and most preferably greater than or equal to about 10:1. On the other hand, simple salts such as sodium chloride can be used without a large adverse effect.

Several of the stabilizing anions of the instant invention, such as saccharinate, acetyltryptophanate and gentisate, can, in fact, provide buffering and ionic strength while at the same time providing the stabilizing effect reported herein, minimizing or eliminating the need for other buffers (which might introduce destabilizing compounds). This is in fact another reason why anions with very low pKa's are disfavored in this invention, because they cannot effectively buffer solutions against pH change, and may thus require other anions, which could be detrimental anions. For a given ionic strength (or buffer strength) target, one can calculate the amount of saccharin, NAT, gentisate or other stabilizing anion of the invention that is needed to establish that ionic (or buffer) strength, according to formulae that are well known to one skilled in the art. The counterion to the stabilizing anion in such a case could be selected to be an organic cation (or base), such as ethanolamine, diethanolamine, triethanolamine, ammonium, or tromethamine. It should be noted that there is a fundamental difference between this anion-cation counterion relationship, which preserves the stabilizing effect of the stabilizing anion, and molecules in which anionic and cationic groups are present on the same molecule, in a zwitterionic compound such as an amino acid, which are not stabilizing in this invention. The distinction between salts and zwitterions is well known in the art.

In an embodiment of the invention which is a water-containing solution of a protein or peptide, the stabilizing anions, taken together, will generally be at a significant molar excess to the drug—or more precisely, to the moles of asparaginyl groups on the drug molecules. That is, in cases, such as insulin, where the drug has more than one asparaginyl residue, the molar ratio should be calculated as the total number of moles of the stabilizing anion or anions, divided by the total number of moles of asparagine residues on the drug molecules; the latter is calculated by multiplying the number of moles of drug by the number of asparagine residues per molecule. The preferred molar excess (calculated by subtracting unity from this molar ratio and multiplying by 100%) will preferably be greater than or equal to about 100% (i.e., molar ratio of 2:1), and more preferably greater than or equal to about 200% (3:1), and most preferably greater than about 800% (9:1).

A hydrophobic group on the anion, such that the anion has at least 6 carbon atoms most preferably in a contiguous hydrophobic group, can improve binding of, or association of, the anionic compound with hydrophobic moieties in the protein or peptide, enhancing subsequent stabilization by a combination of one or more effects, including: A) a hydrophobic interaction with the hydrophobic portion of the drug; B) a reduced translational entropy and thus tighter binding to drug due to higher molecular weight than, say, an atomic cation or an amino acid; C) the creation of a sufficiently hydrophobic local environment (and thus a "drier" milieu) at the site of the labile group, upon associating with the drug and/or with other anions associated with the drug; and D) a reduced partitioning into water domains, in systems comprising water-lean domains by virtue of other additives. One or more of these factors may account for the results of Example 2 herein, where N-acetyltryptophan was shown to have a dramatic stabilizing effect on one deamidation-susceptible peptide.

The current invention could allow PLGA-based encapsulation to be used with proteins and other molecules for which it currently cannot be used. A limiting problem with PLGA is that as it erodes so as to release drug, it releases lactic acid (and/or glycolic acid), a strong acid that produces low pH in the local vicinity, potentially breaking down via hydrolysis the very drug the polymer was designed to protect. One way to use the invention to circumvent this problem is to encapsulate, along with the drug pharmaceutical ingredient, one of the organic anions of the current invention. The invention could protect not only against hydrolysis of the peptide bonds, but also against deamidation and other hydrolysis reactions that occur with proteins, particularly at acidic pH. As such, this approach could potentially be enabling for many proteins and peptides that cannot be formulated together with PLGA. Salts of saccharin and these other preferred organic acids of the invention act as buffers, so they can keep the local pH from becoming too acidic. Gentisic acid and saccharin are preferred in this respect. Because of the organic and amphiphilic character of these organic acids of the invention, in an emulsion-based encapsulation process, typically the stabilizer will preferentially go into the organic phase, which is what forms the microparticles; dropping the pH at the stage in the process where partitioning into the organic phase is desired would aid this. This organic-phase partitioning may be found to hold for a particular organic anion stabilizer even in cases where the stabilizer is added as a salt, and is more likely if the counterion to the organic anion is also organic, rather than sodium or potassium or the like; indeed, organic counterions are generally preferred over inorganic counterions in the practice of this invention. Thus, without undue work one should be able to encapsulate a substantial fraction of the stabilizer in the microparticles. Organic anion stabilizer adsorbed to the surface of the microparticles may also contribute to drug stabilization, though generally to a lesser extent. As the PLGA erodes and the protein becomes subject to conditions created by the lactic acid by-product, the organic stabilizer is present in the immediate environment, to help stabilize both pH and the hydrolyzable bonds on the active pharmaceutical ingredient.

As stated above, peptides and proteins themselves are generally not stabilizing anions, due to protic amino (and often additional) groups present that render the compound zwitterionic instead of anionic, and/or may be detrimental nucleophiles and counter the effect of any stabilizing nucleophilic anions such as saccharin, etc. However, since proteins and peptide actives can have cationic groups on them, it may be possible to apply the current invention in a way that takes advantage of these cationic groups on the peptide drug (such as amino groups in lysine residues of the peptide drug, etc.). In particular, the stabilizing anions of the invention could be ionically bound—as counterions—to cationic groups on the peptide or protein drug, instead of the usual chloride or other counterions that result from salts and buffer components. Care would be taken in such cases to minimize the use of salts or buffers containing chloride, bromide, acetate or other anions.

As illustrated in Example 3 below, the effectiveness of the invention can be demonstrated, and to some extent quantified, by the use of NMR. While there are a number of specific NMR-based methods one skilled in the art can imagine, one straightforward method is to use proton NMR to look for electron distribution changes in the neighborhood of the asparaginyl carbonyl carbon that is the target of nucleophilic attack in deamidation. In particular, the $^1$H NMR chemical shift of the hydrogens on the beta carbon of a deamidation-susceptible asparaginyl residue will be seen to move upfield in a solution that uses the invention to inhibit deamidation of that residue. Preferably this upfield movement will be at least about 10 ppb, and more preferably at least about 20 ppb, and the same is true for the two hydrogens on the side-chain amide (in particular, the $NH_2$) of asparagine. Indeed, any compound that causes an upfield shift greater than or equal to about 10 ppb, or more preferably greater than or equal to about 20 ppb, in these protons is a stabilizer that can be used in the current invention. Carbon NMR of the carbonyl carbon would be a slightly more difficult, but more direct, indicator of stabilizer effectiveness. As shown in Example 3, the main-chain nitrogen on the adjacent amino acid is relatively less directly affected by stabilizers of the invention than those groups on the asparaginyl side chain; this position is affected primarily by a competitive mechanism, with respect to the carbonyl-stabilizer interaction.

The invention is particularly useful in stabilizing a protein or peptide in which one or more asparaginyl residues is flanked on its C-terminal side by either a glycinyl or serinyl residue. Such is the case with a number of known deamidation-susceptible, and deamidation-prone, proteins and peptides. Human tissue plasminogen activator has Asn-Ser sequences at sites 37 and 177, as well as an Asn-Gly sequence at site 58, for example. Calmodulin has Asn-Gly sequences, as do angiogenin, many RNases, hirudin, neuropeptide S, aldolase, calbindin, fatty acid binding protein, fibroblast growth factor, glucoamylase, interleukin 1β, lysozyme, T-cell surface glycoprotein CD4, triose phosphate isomerase, trypsin, phosphocarrier protien Hpr, and hemoglobin; human epidermal growth factor and growth hormone have one and two susceptible Asn-Ser sequences, resp. Three sites of deamidation under relatively mild conditions have been determined for both horse heart cytochrome c and the recombinant hirudin variant rHV2-Lys47. [See Bishoff R and Kolbe H V J (1994) J. Chrom. B, 662:261]. The invention can be useful in all these cases.

The current invention can provide ready-to-use, pharmaceutically-acceptable for injection, aqueous formulations of therapeutic proteins that fall into the five drug classes of erythropoietins, insulins, colony-stimulating factors, interferons, and monoclonal antibodies. The active pharmaceutical ingredients in these classes depend on specific interactions to perform their therapeutic functions, and thus deamidation of such a protein or peptide is generally far more consequential than in the case of a protein that functions primarily via non-specific interactions such as hydrophobic interaction or volume replacement. With monoclonal antibodies, the asparagine residue Asn55, for example, located in the CDR2 region of the heavy chain is prone to non-enzymatic deamidation, and deamidation at this site often greatly reduces binding activity. Thus the invention can be particularly useful in limiting deamidation of therapeutic and prophylactic antibodies.

Use of stabilizing anions as disclosed herein could be used to stabilize aqueous solutions of proteins and peptides such that, for example, they can then be supplied as ready-to-use formulations, preferably with at least 2 years shelf-life. This can be of particular value in cases where the drug is used in emergency situations, operating suites, and where the drug is given by self-administration by non-medical lay persons such as in home use situations. Indeed, a drug that currently must be given in a clinical setting because of the need for reconstitution may, by application of this invention, be made available for home use. The dangers inherent in intravenous injection of reconstituted powders should not be underestimated, since any undissolved material (resulting, e.g., from insufficient shaking after addition of sterile water) can lead to emboli and cannot always be easily seen by the untrained eye; furthermore, it is well known that many drug formulations intended for non-intravenous routes of administration can sometimes be inadvertently injected intravenously or intra-arterially, and the current invention can help prevent these.

As seen in the following table, a great many human proteins have storage times less than 2 years in aqueous solution (here pH 7.4 and 37° C. Tris-HCl buffer), meaning that they degrade 10% in less than two years, so that the invention could be advantageous to apply in the case of these proteins and peptides. The half-life in days is given in the column labeled $T_{1/2}$, and the time to 10% degradation by deamidation is given in the column labeled $T_{1/10}$, and thus any protein with less than 104 in the $T_{1/10}$ column is not pharmaceutically-acceptable for injection for two years storage life under these conditions. Thus, these proteins may be formulated according to the invention, and potentially made pharmaceutically-acceptable for injection under a shelf-life requirement of two years; the probability of success is substantial with $T_{1/10}$ values of greater than about 15 days, which are bolded in the table. Also, some of the proteins with $T_{1/10}$ less than 15 days might be amenable to formulation as stable aqueous solutions of the invention if the storage temperature is stipulated as refrigerator temperature, and/or if the pH of the formulation is set at somewhat more extreme values than the most preferred range of 4 to 9. In addition, a protein or peptide with a $T_{1/10}$ value less than about 1 day might benefit by using the invention in the form of a stabilizer incorporated into a lyophilized powder containing the protein/peptide, or into an aqueous solution used to reconstitute the protein/peptide.

| Human protein | $T^{1/2}$ | $T^{1/10}$ |
| --- | --- | --- |
| Uracil-DNA glycosylase (1LAU) | 1.0 | 0.15 |
| Uroporphyrinogen decarboxylase (1URO) | 1.0 | 0.15 |
| Transaldolase (1F05) | 1.4 | 0.21 |
| Urokinase-type plasminogen activator (1LMW) | 1.7 | 0.26 |
| Purine nucleoside phosphorylase (1ULA) | 1.8 | 0.27 |
| Growth hormone receptor (1A22) | 2.4 | 0.36 |
| Peptidyl-prolyl cis-trans isomerase (1F8A) | 2.4 | 0.36 |
| Thymidylate synthase (1HW3) | 2.7 | 0.41 |
| Procathepsin B (3PBH) | 2.9 | 0.44 |
| D-Glyceraldehyde-3-phosphate dehydrogenase (3GPD) | 4.2 | 0.64 |
| Karyopherin 2 (1QBK) | 5.3 | 0.81 |
| Glutathione S-transferase (12GS) | 5.3 | 0.81 |
| N-acetylgalactosamine-4-sulfatase (1FSU) | 6.1 | 0.93 |
| Fructose bisphosphate aldolase (4ALD) | 7.6 | 1.2 |
| Intestinal fatty acid binding protein (3IFB) | 7.6 | 1.2 |
| Cyclophilin A (1AWQ) | 8.7 | 1.3 |
| Vascular endothelial growth factor (2VPF) | 10 | 1.5 |
| Inositol monophosphatase (1IMB) | 15 | 2.3 |
| Pancreatic inhibitor variant 3 (1CGI) | 16 | 2.4 |
| D-Glucose 6-phosphotransferase (1HKC) | 16 | 2.4 |
| Myeloperoxidase (1MHL) | 16 | 2.4 |
| -Chymotrypsinogen (1CGI) | 16 | 2.4 |
| Lysophospholipase (1LCL) | 16 | 2.4 |
| Interleukin-16 (1I16) | 17 | 2.6 |
| C-AMP-dependent kinase A (1CMK) | 19 | 2.9 |
| Pepsinogen (1HTR) | 20 | 3.0 |
| Angiogenin (1A4Y) | 21 | 3.2 |
| Fibroblast growth factor (2AFG) | 21 | 3.2 |
| Calmodulin (1CTR) | 21 | 3.2 |
| Bone morphogenetic protein 7 (1BMP) | 21 | 3.2 |
| Acetylcholinesterase (1F8U) | 23 | 3.5 |
| Retinol binding protein (1BRQ) | 24 | 3.6 |
| Catalase (1QQW) | 25 | 3.8 |
| Dihydrofolate reductase (1DRF) | 25 | 3.8 |
| Interleukin-10 (2ILK) | 25 | 3.8 |
| Farnesyltransferase (1EZF) | 26 | 4.0 |
| S-adenosylhomocysteine hydrolase (1A7A) | 28 | 4.3 |
| Procathepsin K (1BY8) | 28 | 4.3 |
| 3-Methyladenine DNA glycosylase (1BNK) | 35 | 5.3 |
| Medium chain acyl-coa dehydrogenase (1EGE) | 36 | 5.5 |
| Homeobox protein PAX-6 (6PAX) | 39 | 5.9 |
| 1-Antitrypsin (1QLP) | 40 | 6.1 |
| Carbonic anhydrase I (1HCB) | 45 | 6.8 |
| GTP-binding protein (1DOA) | 45 | 6.8 |
| Ferritin (2FHA) | 46 | 7.0 |
| Procathepsin L (1CS8) | 48 | 7.3 |
| Growth hormone (1HGU) | 51 | 7.8 |
| Triose phosphate isomerase (1HTI) | 52 | 7.9 |
| Interleukin-6 (1IL6) | 56 | 8.5 |
| DNA polymerase (1BPX) | 58 | 8.8 |
| Glutathione synthetase (2HGS) | 58 | 8.8 |
| Fructose-1,6-bisphosphatase (1FTA) | 59 | 9.0 |
| CDK2 kinase (1BUH) | 65 | 9.9 |
| Ribonuclease A (1AFK) | 66 | 10 |
| Ap endonuclease (1BIX) | 72 | 11 |
| Carbonic anhydrase IV (1ZNC) | 72 | 11 |
| Branched-chain -keto acid dehydrogenase (1DTW) | 81 | 12 |
| Argininosuccinate lyase (1AOS) | 83 | 13 |
| Creatine kinase (1QK1) | 84 | 13 |
| Carbonic anhydrase II (1BV3) | 90 | 14 |

-continued

| Human protein | T½ | T¹⁄₁₀ |
|---|---|---|
| Interleukin-8 (1IL8) | 95 | 14 |
| Dihydropteridine reductase (1HDR) | 100 | 15 |
| Proinsulin (1EFE) | 110 | 17 |
| Mitogen-activated protein kinase P38 (1WFC) | 110 | 17 |
| Glutathione reductase (1BWC) | 120 | 18 |
| Ribonuclease 4 (1RNF) | 130 | 20 |
| Aldose reductase (1EL3) | 130 | 20 |
| -Lactalbumin (1B9O) | 130 | 20 |
| Ornithine transcarbamoylase (1OTH) | 130 | 20 |
| Malic enzyme (1EFK) | 140 | 21 |
| Glucose-6-phosphate 1-dehydrogenase(1QKI) | 140 | 21 |
| Procarboxypeptidase A2 (1AYE) | 150 | 23 |
| Apoptosis regulator bax (1F16) | 170 | 26 |
| Ornithine decarboxylase (1D7K) | 170 | 26 |
| UDP-galactose 4-epimerase (1EK6) | 180 | 27 |
| Stem cell factor (1EXZ) | 180 | 27 |
| Hypoxanthine guanine phosphoribosyltransferase (1BZY) | 180 | 27 |
| Electron transfer flavoprotein (1EFV) | 190 | 29 |
| Phenylalanine hydroxylase (1DMW) | 220 | 33 |
| Annexin V (1ANX) | 220 | 33 |
| Platelet factor 4-HPF4 (1RHP) | 230 | 35 |
| Insulin (2HIU) | 260 | 40 |
| Prethrombin2 (1HAG) | 260 | 40 |
| Interleukin-4 (2CYK) | 270 | 41 |
| Interleukin-1 (2I1B) | 280 | 43 |
| Neutrophil (gelatinase) (1DFV) | 290 | 44 |
| O6-alkylguanine-DNA alkyltransferase (1EH6) | 300 | 46 |
| Glucosamine-6-phosphate deaminase isomerase (1D9T) | 320 | 49 |
| Quinone reductase type 2 (1QR2) | 330 | 50 |
| NAD(P)H dehydrogenase (1QBG) | 350 | 53 |
| Plasminogen activator inhibitor-1 (1C5G) | 370 | 56 |
| T cell surface glycoprotein CD4 (1CDJ) | 380 | 58 |
| -Thrombin (1A3E) | 380 | 58 |
| Eosinophil cationic protein (1QMT) | 430 | 65 |
| Ribonuclease inhibitor (1A4Y) | 450 | 68 |
| Transforming growth factor-two (1KLA) | 460 | 70 |
| Thioltransferase (1JHB) | 470 | 71 |
| Profilin 1 (1FIL) | 480 | 73 |
| Lithostathine (1LIT) | 490 | 74 |
| Phosphatidylethanolamine binding protein (1BD9) | 680 | 100 |

Source of data: Deamidation of Human Proteins, Robinson & Robinson, PNAS Oct. 23, 2001 Vol. 98 No. 22 12409-12413.

Other deamidation-susceptible proteins and peptides that could be protected against deamidation by the present invention, preferably in human or veterinary pharmaceutical or vaccine preparations, include: acid phosphatase; alkaline phosphatase; acidic fibroblast growth factor; amylin praline analog (Pramlintide); angiogenin; antiflammin; antithrombin III; apolipoproteins; aspartate aminotransferase; atrial natriuretic peptide; Bence-Jones protein TI; calbindin; calmodulin; carbonic anhydrase; CD4; cell surface protein G (as in a vaccine, for example); chorionic somatomammotropin; class II histocompatibility antigen; collagen; creatine kinase; dehalogenase; deoxyribonucleases; elastase; envelope glycoprotein E1 (e.g., in a hepatitis C vaccine); epidermal growth factor; fibroblast growth factor; glucagon and glucagon-like peptides; glucose-6-phosphate dehydrogenase; glucose-6-phosphate isomerase; glutathione S-transferase; granulocyte-colony-stimulating factor; growth hormone releasing factor; hexokinase; hexon protein; HMAP; high MW glycoprotein (e.g., from skin fibroblasts); hirulog-3-thrombin complex; histone; HIV-1 Rev; hypoxanthine-guanine phosphoribosyl-transferase; inorganic pyrophosphatase; interferon; interleukins 1, 2, 3, and 11; interleukin-1 receptor antagonist; lactate dehydrogenase; lactoferrin; L-alanine:2-oxoglutarate aminotransferase; leukaemia protein P30 (e.g., in a vaccine); lysozyme; macrophage migration inhibitory factor; major internal protein of SKA virus; major intrinsic protein MP26; membrane protein 4.1; beta-2-microglobulin; myoglobin; N-acetyl-beta-D-glucosaminidase; NAD(P)H dehydrogenase; nerve growth factor; neu differentiation factor; neurotrophic factor; neutrophil activating peptide; nucleoside phosphorylase; parathyroid hormone; parotid basic proteins Pb-1a, Pb-1b and Pb2; phenylalanine hydroxylase; phosphoglucomutase; 6-phospo-D-gluconate dehydrogenase; plasminogen activator; prolactin; rotavirus protein VP6; staph aureus protein A; prothymosin; purine-nucleoside phosphorylase; retinol-binding protein; rhinovirus-14 3C protease; somatomedin A (insulin-like growth factor); stem cell factor; thioltransferase; thrombopioetin; transmembrane secretory component; tumor necrosis factor; uropepsinogen and uropepsin; vascular endothelial growth factor; and vasopressin. It should be noted that, in addition to the possibilities of some of these compounds as active pharmaceutical compounds, some of them could be useful in pharmaceutical preparations as targeting compounds, to target specific cells, cells with specific disorders, or even pathogens in the body.

Vaccines are another class of formulations wherein deamidation of proteins in the formulation can have serious negative consequences, and wherein the current invention could be applied. In the context of this invention, vaccines differ from traditional pharmaceutical and even biopharmaceutical products in that they are considerably more likely to contain at least trace levels of enzymes that can induce enzymatic deamidation. Thus, while protecting proteins and peptides against non-enzymatic deamidation is the main focus of this invention, it may nonetheless be true that the invention could protect against enzymatic deamidation during production and/or storage of a vaccine formulation. If the interpretation above is reasonably correct, then a complex or intermittent covalent bond between stabilizer and labile site would also be expected to limit enzymatic deamidation, by a sort of competitive inhibition at the labile site. Enzymatic deamidation is believed to occur in certain hepatitis vaccines, for example.

Hemoglobin is known to undergo nonenzymatic deamidation, and while it is not a traditional active pharmaceutical ingredient, it is being investigated as a key ingredient in artificial blood (blood substitute), and thus formulations containing hemoglobin or related heme protein for blood substitutes are within the scope of this invention.

Embodiments of the current invention can be used for many routes of administration compatible with peptide or protein delivery, including but not limited to parenteral, intravenous, intraperitoneal, intrathecal, intramuscular, subcutaneous, intra-arterial, rectal, intravaginal, sublingual, intraocular, transdermal, intranasal, via inhalation, in a suppository, ophthalmic, and others. Oral delivery of peptides and proteins is currently a largely unsolved problem, although several promising approaches have made progress, and the invention may be compatible with some such formulations.

It should be noted that while the primary function of the current invention is to minimize or prevent deamidation, other degradation reactions occurring in the formulations of the invention might also be concomitantly reduced by the stabilizing anion(s). This is particularly true for other base-catalyzed reactions involving carbonyl groups.

EXAMPLES

Example 1

A deamidation-prone decapeptide with two labile asparaginyl residues was shown in this Example to be stabilized against deamidation by the current invention; the Example also shows the destabilizing effect of anions such as acetate and phosphate. To begin with, a decapeptide was synthesized by request at the Protein Facility of the Iowa State University Office of Biotechnology, using standard peptide synthesis methodology. The peptide had the sequence RCNSGR-FNGG-NH$_2$ (Arg-Cys-Asn-Ser-Gly-Arg-Phe-Asn-Gly-Gly, terminal amide). Literature on peptide degradation by deamidation at asparagine sites shows by overwhelming consensus that the FNG and CNS subsequences are prone to degradation.

Samples containing this decapeptide were prepared under eight different conditions at two different pH values, pH 7 and 4. The 200 mM arginine/100 mM phosphate buffer was only prepared at pH 7. The preparation of these samples is now described. The ratios indicated are molar ratios of organic anion to decapeptide.

HCl-Control. Into a sterile 15 mL plastic centrifuge tube (Corning Incorporated, Corning, N.Y.) was placed 0.0021 g decapeptide (Iowa State University, Ames, Iowa) and 7.0 g sterile water (Spectrum Chemicals Mfg. Corp., Gardena, Calif.). The pH was adjusted using 1.0N HCl (Spectrum Chemicals Mfg. Corp., Gardena, Calif.) to a pH of 4. Into a new 15 mL plastic centrifuge tube was placed 3.5 mL of a pH 4 solution. The pH was adjusted using only the necessary amount of 1.0N NaOH (Spectrum Chemicals Mfg. Corp., Gardena, Calif.) to a final pH of 7.

Saccharin: decapeptide, 1:1 (anion:asparaginyl molar ratio). Into a sterile 15 mL plastic centrifuge tube was placed 0.0021 g decapeptide, 0.0011 g sodium saccharin (Spectrum Chemicals Mfg. Corp., Gardena, Calif.) and 7.0 g sterile water. The pH was adjusted using only the necessary amount of saccharin (Spectrum Chemicals Mfg. Corp., Gardena, Calif.) to a pH of 4. Into a new 15 mL plastic centrifuge tube was placed 3.5 mL of a pH 4 solution. The pH was adjusted using only the necessary amount of 1.0N NaOH to a final pH of 7.

Saccharin: decapeptide, 3:1. Into a sterile 15 mL plastic centrifuge tube was placed 0.0021 g decapeptide, 0.0029 g sodium saccharin and 7.0 g sterile water. The pH was adjusted using only the necessary amount of saccharin to a pH of 4. Into a new 15 mL plastic centrifuge tube was placed 3.5 mL of a pH 4 solution. The pH was adjusted using only the necessary amount of 1.0N NaOH to a final pH of 7.

Saccharin: decapeptide, 10:1. Into a 15 mL plastic centrifuge tube was placed 0.0021 g decapeptide, 0.0095 g sodium saccharin and 7.0 g sterile water. The pH was adjusted using only the necessary amount of acid saccharin to a pH of 4. Into a new 15 mL plastic centrifuge tube was placed 3.5 mL of a pH 4 solution. The pH was adjusted using only the necessary amount of 1.0N NaOH to a final pH of 7.

Acetate: decapeptide, 3:1. Into a sterile 15 mL plastic centrifuge tube was placed 0.0021 g decapeptide, 0.0016 g sodium acetate (Spectrum Chemicals Mfg. Corp., Gardena, Calif.) and 7.0 g sterile water. The pH was adjusted using only the necessary amount of acetic acid (Spectrum Chemicals Mfg. Corp., Gardena, Calif.) to a pH of 4. Into a new 15 mL plastic centrifuge tube was placed 3.5 mL of a pH 4 solution. The pH was adjusted using only the necessary amount of 1.0N NaOH to a final pH of 7.

Acetate/Saccharin: decapeptide, 3/10:1. Into a sterile 15 mL plastic centrifuge tube was placed 0.0021 g decapeptide, 0.0016 g sodium acetate, 0.0094 g sodium saccharin and 7.0 g sterile water. The pH was adjusted using only the necessary amount of acid saccharin to a pH of 4. Into a new 15 mL plastic centrifuge tube was placed 3.5 mL of a pH 4 solution. The pH was adjusted using only the necessary amount of 1.0N NaOH to a final pH of 7.

Into a sterile 1.5 mL microcentrifuge tube was placed a 0.5 g portion of each sample condition and were placed at −18° C. This was the initial sample. The remaining pH 4 samples were placed at 65° C. until completion of the experiment. The remaining pH 7 samples were placed at 40° C. until completion of the experiment. Into a sterile 1.5 mL microcentrifuge tube was placed a 0.5 g portion of each sample condition on "day 1", 24 hours after preparation, and were placed at −18° C. This was the day 1 sample. The frozen initial and day 1 samples were thawed to room temperature, and assayed using HPLC.

Chromatographic analysis. The samples at the various timepoints were then analyzed with HPLC using the following conditions.
System: Schimadzu SCL-10A VP with diode array detector
Column: Phenomenex C18 Luna 5 um, 250×4.6 mm
Mobile Phase: Isocratic 90% (0.1%) TFA in water, 10% (0.08%) TFA in acetonitrile
Flow Rate: 1.0 mL/min
Wavelength: 214 nm The potency (mg/mL of intact peptide) was determined by integrating under this peak (performed by the instrument), and normalizing according to a standard run of the decapeptide. The relative potency was then calculated by dividing the potency at the given timepoint by the initial potency, thus giving the fraction of the original potency that still remained after the 1 day, or 4 day, period at the stress temperature (40° C. or 65° C.).

Results. The pH 7 samples were first analyzed, and the results are summarized in the table below.
Table of relative potencies after 24 hours at 40° C. Note that the molar ratio of acid to asparaginyl groups, given in the middle column, is half the molar ratio of acid to decapeptide, because there are two asparaginyl residues in the decapeptide.

| Acid(s) | Molar ratio anion:Asn | Relative potency |
|---|---|---|
| Hydrochloric | N/A | 0.067 |
| Acetate | 3 | 0.001 |
| Saccharin/Acetate | 10/3 | 0.166 |
| Saccharin | 1 | 0.080 |
| Saccharin | 3 | 0.008 |
| Saccharin | 10 | 0.523 |

As can be seen from the table, the control (HCl), acetate, and arginine/phosphate samples almost completely degraded, with less than 7% potency remaining in the HCl case, and only 0.1% or less in the cases of the destabilizing anions acetate and phosphate. (This is the aqueous buffer used in currently marketed formulations of tissue plasminogen activator).

In contrast, over 50% retained in the 10:1 saccharin:asparagine sample. Furthermore, the addition of the destabilizing anion acetate, at 3:1 acetate:asparargine, dropped the relative potency of the 10:1 saccharin sample down from this 52% to only 16.6%. This demonstrates the effect of a destabilizing anion in severely inhibiting, or negating, the beneficial effect of a stabilizing anion such as saccharin—even at a ratio of destabilizing anion to stabilizing anion of only 3:10=0.3 (i.e., a molar ratio of stabilizing anion to destabilizing anion of 3.33:1).

For the samples at pH 4, the relative potencies were highest after 24 hours in the case of saccharin 10:1 (87% relative potency). Thus, saccharin was a very effective stabilizer at this pH of 4.

Example 2

The same decapeptide as in Example 1 was then tested with other stabilizing and destabilizing anions. The sample stressing and HPLC were applied as above.

N-acetyltryptophan: decapeptide, 3:1 (anion:asparaginyl ratio). Into a sterile 15 mL plastic centrifuge tube was placed 0.0021 g decapeptide, 0.0029 g N-acetyl-D-tryptophan (MP Biomedicals, Solon, Ohio) and 7.0 g sterile water. The pH was adjusted using 1.0N HCl to a pH of 4. Into a new 15 mL plastic centrifuge tube was placed 3.5 mL of a pH 4 solution. The pH was adjusted using only the necessary amount of 1.0N NaOH to a final pH of 7. Since the molar ratio of acetyltryptophan to decapeptide is 6:1, and each decapeptide has two asparaginyl residues, the molar ratio of NAT to asparagine is 3:1.

Decapeptide in 200 mM arginine/100 mM phosphate buffer. Into a sterile 15 mL plastic centrifuge tube was placed 0.3487 g L-arginine (Spectrum Chemicals Mfg. Corp., Gardena, Calif.), 0.0014 g monosodium phosphate (Spectrum Chemicals Mfg. Corp., Gardena, Calif.), 0.0098 g sodium phosphate dibasic anhydrous (ICN Biomedicals, Inc., Auroa, Ohio) and 10.0 g sterile water. Into a new 15 mL plastic centrifuge tube was placed 3.5 mL of a 200 mM arginine/100 mM phosphate buffer and 0.0011 g decapeptide. The pH was adjusted using only the necessary amount of 1.0N NaOH to a final pH of 7. One can calculate that the approximate molar ratio of phosphate ions to asparaginyl residues is about 223:1.

| Acid(s) | Molar ratio anion:Asn | Relative potency |
| --- | --- | --- |
| Hydrochloric | N/A | 0.067 |
| Phosphate | 223 | 0 |
| N-acetyltryptophanate | 3 | 1.028 |

In sharp contrast to the hydrochloric control, and with the complete loss of potency in the phosphate/arginine buffer, the potency has been completely retained in the sample containing the stabilizing anion N-acetyltryptophan. For the samples stressed at pH 4, the acetyltryptophan was the highest among these three, with 74% potency remaining.

High-MW compounds such as proteins, and even peptides, exhibit strong steric effects that are known to be of importance in, among other things, deamidation. For instance, steric effects could greatly inhibit the effect of a stabilizing compound (particularly one of higher MW) on a labile peptide or protein, by interfering with the necessary intimacy between the stabilizer and the labile chemical group. The labile group could in effect be tucked away so as to be "hidden" from the stabilizer, yet still susceptible to the destabilizing effect of the nucleophile, which in the typical deamidation reaction is immediately present in the next residue. Nevertheless, this Example shows that the present invention can be extremely powerful and effective in protecting peptides from deamidation.

FIG. 1 graphically summarizes data in Examples 1 and 2. Specifically, FIG. 1 graphically represents the potency retention data for the decapeptide accelerated stability test of the invention. The height of each bar gives the concentration, in mg/mL, of intact decapeptide after stressing, as measured by HPLC, with the initial concentration approximately 1.0 mg/mL in each case and at the same pH of 7.0. Thus, the solution of decapeptide in the hydrochloric acid control sample (unbuffered) has been reduced to just under 7% of its original potency, etc. The N-acetyltryptophan sample of the invention shows no detectable degradation, and the saccharin samples show enhanced stability at a saccharin:peptide molar concentration of 20:1, and much less enhancement at only 2:1 (and thus 10:1 and 1:1, resp., of saccharin:asparaginyl residues). The bar labeled Saccharin-Acetic demonstrates how the presence of a detrimental anion (acetate) can limit or even ruin the stability enhancement of a stabilizing anion (saccharinate).

Example 3

In this Example, the decapeptide from Example 1 was examined by $^1$H NMR in a solution according to the invention, and compared to a control solution without stabilizer.

HCl-Control. To a sterile 1.5 mL microcentrifuge tube was placed 0.0005 g decapeptide and 1.0 g $D_2O$ (deuterium oxide; deuterated water). The pH was adjusted using only the necessary amount of 1.0N HCl and 1.0N NaOH to a final pH of 7.0.

Acetate: Decapeptide, 4:1. To a sterile 1.5 mL microcentrifuge tube was placed 0.0005 g decapeptide, 0.0006 g sodium acetate, and 1.0 g $D_2O$. The pH was adjusted using only the necessary amount of 1.0N NaOH to a final pH of 7.0.

Saccharin: Decapeptide. 4:1. To a sterile 1.5 mL microcentrifuge tube was placed 0.0003 g decapeptide, 0.0006 g sodium acetate, and 1.0 g $D_2O$. The pH was adjusted using only the necessary amount of 1.0N NaOH to a final pH of 6.9.

Immediately following preparation the samples were stored at 4° C. The proton NMR analysis was performed on a 400 MHz NMR spectrometer.

NMR results and analysis. The following chart summarizes the NMR results at positions where peak shifts were seen between peak positions for the control, acetate and saccharin samples. (Peaks corresponding to the stabilizers themselves, namely acetate and saccharin, naturally occurred in only one of the three samples, such as saccharin peaks near 7.7 ppm and acetate peaks near 1.75). The rightmost column gives the distance, in number of intervening bonds, between the proposed position and the nearest of the two reactive groups that can participate in the deamidation reaction, namely the Asn carbonyl and the main-chain nitrogen on the next residue.

| Peak # | Control (ppm) | Acetate (ppm) | Saccharin (ppm) | Acetate from control (ppb) | Saccharin from control (ppb) | Proposed position assignment | Distance from reactive group |
| --- | --- | --- | --- | --- | --- | --- | --- |
| 1a | 3.026 | 3.028 | 2.994 | +2 | −32 | Beta of Asn | 1 |
| 1b | 2.961 | 2.962 | 2.932 | +1 | −19 | (doublet) | |
| 2a | 2.631 | 2.627 | 2.620 | −4 | −11 | Beta of next | 2 |
| 2b | 2.544 | 2.545 | 2.541 | +1 | −3 | residue (Ser) | |

-continued

| Peak # | Control (ppm) | Acetate (ppm) | Saccharin (ppm) | Acetate from control (ppb) | Saccharin from control (ppb) | Proposed position assignment | Distance from reactive group |
|---|---|---|---|---|---|---|---|
| 3 | 4.621 | 4.622 | 4.621 | +1 | 0 | Alpha of Asn | 2 |
| 4a | 7.177 | 7.178 | 7.150 | +1 | −27 | Delta of Asn | 1 |
| 4b | 7.113 | 7.113 | 7.089 | 0 | −24 | (doublet) | |
| 5a | 3.789 | 3.790 | 3.783 | +1 | −6 | Alpha of next residue (Gly) | 1 |
| 5b | 3.761 | 3.763 | 3.750 | +2 | −11 | | |

The predominance of small, usually positive numbers in the "acetate from control" column demonstrate that acetate has no stabilizing effect, and perhaps a slight de-stabilizing effect, on asparagine deamidation. In contrast, the large, negative numbers in the "saccharin from control" column, at least for positions that are adjacent to one of the reaction groups (distance of 1) show that saccharin has a strong stabilizing effect against deamidation. On a finer point, the smaller shifts (−6 and −11) on 5a and 5b relative to the larger shifts on the other adjacent-to-reactive positions (1 and 4) are consistent with the notion that in the protection by saccharin of the nucleophilic attack of the main-chain nitrogen on the Asn side-chain carbonyl, the latter is more affected in terms of electron distribution—that is, the saccharin functions by interacting with the Asn carbonyl, rather than directly on the main-chain nitrogen. The upfield shifts for those positions closest to the reactive carbonyl group that is directly affected by the presence of saccharin are bolded in the table. The large upfield shifts in all four cases are demonstrating the stabilizing effect of saccharin. In terms of Hertz, the chemical shifts of −32, −19, −27 and −24 ppb correspond, respectively, to 9.2, 7.6, 10.8 and 9.6 Hz.

While the invention has described in terms of a number of preferred embodiments, it will be understood by those of skill in the art that the invention can be practiced with modification in the spirit and scope of the appended claims.

The invention claimed is:

1. A method of protecting the primary structure of peptides or proteins which contain one or more asparaginyl or glutaminyl residues with at least one deamidation prone sequence of -Asn-Gly- against non-enzymatic deamidation at at least said deamidation prone sequence, where the peptides or proteins are present in aqueous formulations or lyophylizates, comprising the step of combining said peptides or proteins with one or more stabilizing anions to form a mixture wherein said stabilizing anions are present in a molar excess to the total number of asparaginyl or glutaminyl residues in said peptides or proteins and are in a molar excess to any destabilizing anions in said mixture, wherein said stabilizing anions are organic compounds that are not zwitterionic where each protic group of said stabilizing anion has a pKa ranging from 0.5 to 3.5, wherein destabilizing anions have at least one protic group that has a pKa of less than 0.5 or greater than 3.5, and wherein said stabilizing anions are selected from the group consisting of saccharin, benzenesulfonic acid, gentisic acid, and N-acetyltryptophan.

2. The method of claim 1 wherein said stabilizing anions include saccharin.

3. The method of claim 1 wherein said stabilizing anions are present at a molar excess of at least 3:1 relative to said total number of asparaginyl or glutaminyl residues in said peptides or proteins.

4. The method of claim 1 wherein said mixture includes at least one destabilizing anion and said stabilizing anions are present at a molar excess of at least 3:1 relative to said at least one destabilizing anion.

5. The method of claim 1 wherein said step of combining is performed prior to lyophilization of said mixture.

6. The method of claim 1 wherein said step of combining is performed on or after reconstitution of a dry powder.

7. The method of claim 1 wherein said proteins or peptides are selected from the group consisting of: a vaccine antigen, erythropoietin, insulin, a colony stimulating factor, interferon and a monoclonal antibody.

8. The method of claim 1 wherein said one or more asparaginyl or glutaminyl residues are flanked on their C terminal side by either a glycinyl or serinyl residue.

9. The method of claim 1 wherein said one or more asparaginyl or glutaminyl residues are asparaginyl residues only.

10. A method of protecting the primary, secondary, and tertiary structure of peptides or proteins which contain one or more asparaginyl or glutaminyl residues with at least one deamidation prone sequence of -Asn-Gly- against non-enzymatic deamidation at at least said deamidation prone sequence, where the peptides or proteins are present in aqueous formulations or lyophylizates, comprising the step of combining said peptides or proteins with one or more stabilizing anions to form a mixture wherein said stabilizing anions are present in a molar excess to the total number of asparaginyl or glutaminyl residues in said peptides or proteins and are in a molar excess to any destabilizing anions in said mixture, wherein said stabilizing anions are organic compounds that are not zwitterionic where each protic group of said stabilizing anion has a pKa ranging from 0.5 to 3.5, wherein destabilizing anions have at least one protic group that has a pKa of less than 0.5 or greater than 3.5, and wherein said stabilizing anions are selected from the group consisting of saccharin, benzenesulfonic acid, gentisic acid, and N-acetyltryptophan.

11. A method of protecting the primary and secondary structure of peptides or proteins which contain one or more asparaginyl residues with at least one deamidation prone sequence of -Asn-Gly- against non-enzymatic deamidation at at least said deamidation prone sequence, where the peptides or proteins are present in aqueous formulations or lyophylizates, comprising the step of combining said peptides or proteins with one or more stabilizing anions to form a mixture wherein said stabilizing anions are present in a molar excess to the total number of asparaginyl residues in said peptides or proteins, wherein said stabilizing anions are organic compounds that produce an upfield movement of at least 10 ppb for the hydrogens on the beta carbon of an asparaginyl residue as measured by $^1$H NMR, and wherein said stabilizing anions are selected from the group consisting of saccharin, benzenesulfonic acid, gentisic acid, and N-acetyltryptophan.

12. The method as in claim 1 wherein the rate of non-enzymatic deamidation of said protein or peptide is decreased due to the presence of the stabilizer.

13. The method as in claim 12 wherein said reduction in deamidation rate is due to the formation of a complex between said stabilizer and said asparaginyl residue.

14. The method as in claim 13 where said complex comprises a temporary covalent bond.

15. The method of claim 1 wherein said stabilizing anions include gentisic acid.

16. The method of claim 1 wherein said stabilizing anions include benzenesulfonic acid.

17. The method of claim 10 wherein said stabilizing anions include saccharin.

18. The method of claim 10 wherein said stabilizing anions include gentisic acid.

19. The method of claim 10 wherein said stabilizing anions include benzenesulfonic acid.

20. The method of claim 10 wherein said stabilizing anions include N-acetyltryptophan.

21. The method of claim 1 wherein said stabilizing anions include N-acetyltryptophan.

* * * * *